(12) United States Patent
Kim et al.

(10) Patent No.: US 6,376,680 B1
(45) Date of Patent: Apr. 23, 2002

(54) PROCESS FOR THE PREPARATION OF 3-ISOTHIAZOLONE MIXTURE AND COMPOSITION COMPRISING THE MIXTURE

(75) Inventors: Jin-Man Kim; Jin-Soo Lim; Seung-Hwan Kim, all of Kyonggi-do; Soon-Jong Hahn, Seoul, all of (KR)

(73) Assignee: SK Chemicals Co., Ltd. (KR)

( * ) Notice: Subject to any disclaimer, the term of this patent is extended or adjusted under 35 U.S.C. 154(b) by 0 days.

(21) Appl. No.: 09/866,009

(22) Filed: May 24, 2001

Related U.S. Application Data

(60) Continuation-in-part of application No. 09/325,488, filed on Jun. 3, 1999, now abandoned, which is a continuation-in-part of application No. 08/964,033, filed on Nov. 4, 1997, now abandoned, which is a division of application No. 08/721,518, filed on Sep. 26, 1996, now abandoned.

(30) Foreign Application Priority Data

Dec. 21, 1995 (KR) .............................................. 95-53412

(51) Int. Cl.$^7$ ............................................. C07D 275/03
(52) U.S. Cl. ....................................... 548/213; 564/192
(58) Field of Search ........................... 548/213; 564/192

(56) References Cited

U.S. PATENT DOCUMENTS 3,849,430 A * 11/1974 Lewis et al.
3,870,795 A * 3/1975 Miller et al.

\* cited by examiner

*Primary Examiner*—T. A. Solola
(74) *Attorney, Agent, or Firm*—Anderson Kill & Olick, PC

(57) ABSTRACT

An impurity-free biologically active mixture of 2-methyl-4-isothiazolin-3-one and 5-chloro-2-methyl-4-isothiazolin-3-one, which is useful as a biocide in various products, can be prepared by reacting N-methyl-3-mercaptopropionamide or N,N'-dimethyl-3,3'-dithiodipropionamide or a mixture thereof dissolved in a first organic solvent with sulfuryl chloride dissolved in a second organic solvent, which is different from the first organic solvent, at a temperature ranging from 5 to 20° C. and, optionally, centrifuging the resulting product mixture to obtain the desired mixture substantially free of 4,5-dichloro-2-methyl-4-isothiazolin-3-one impurity.

13 Claims, No Drawings

PROCESS FOR THE PREPARATION OF 3-ISOTHIAZOLONE MIXTURE AND COMPOSITION COMPRISING THE MIXTURE

CROSS REFERENCE TO RELATED APPLICATION

This application is a continuation-in-part (CIP) application of U.S. Ser. No. 09/325,488 filed on Jun. 3, 1999, now abandoned which is a CIP application of U.S. Ser. No. 08/964,033 filed on Nov. 4, 1997, now abandoned which is a divisional application of U.S. Ser. No. 08/721,518 filed on Sep. 26, 1996, now abandoned.

FIELD OF THE INVENTION

The present invention relates to a process for the preparation of 3-isothiazolone mixture free of 4,5-dichloro-2-methyl-4-isothiazolin-3-one impurity, useful for stabilized isothiazolone compositions.

BACKGROUND OF THE INVENTION

Many 3-isothiazolones are biologically active antimicrobial agents which exhibit biocidal activities towards many microbes such as fungi, bacteria, algae and the like. In particular, a mixture of 2-methyl-4-isothiazolin-3-one of formula (I) and 5-chloro-2-methyl-4-isothiazolin-3-one of formula (II) is known as an effective biocide having both excellent stability and long-lasting activity, and commercially used as preservatives in various products such as paints, cosmetics, surfactants, agricultural chemicals, food additives and the like.

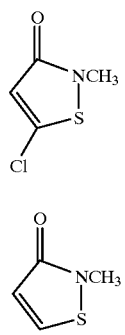

The isothiazolone compounds exhibit potent activities when they are employed in the form of a mixture thereof owing to a synergistic effect. The activity of the mixture depends on the mix ratio, and is known to be maximized when the content of the compound (II) is higher than that of the compound (I). Many efforts have been, therefore, made to develop an improved process for preparing an effective mixture of the compounds (I) and (II). Most prior methods are directed to effectively control or remove nitrosamine precursors generated during the preparation of the mixture of the compounds (I) and (II) using a disulfide compound as the starting material.

However, a mixture of the compounds (I) and (II) prepared in accordance with a conventional method contains 4,5-dichloro-2-methyl-4-isothiazolin-3-one of formula (III) as an inactive component:

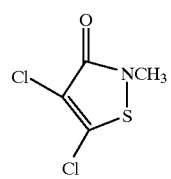

Reaction Scheme 1, shown below, represents a process for preparing a mixture of the compounds (I) and (II) using a disulfide compound as the starting material, e.g., as is disclosed in EP Patent No. 95,907:

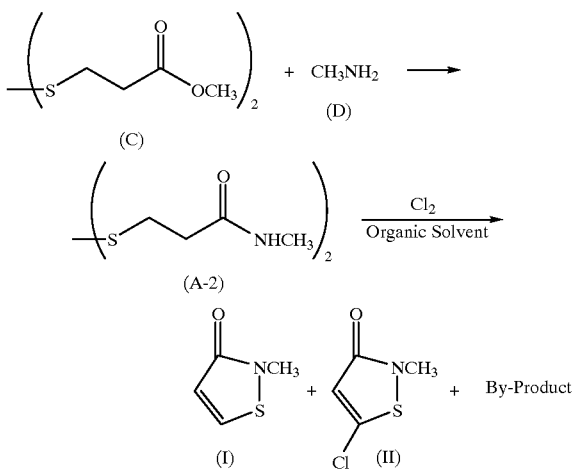

In Reaction Scheme 1, a disulfide compound of formula (C) is amidated with methylamine of formula (D) to obtain N,N'-dimethyl-3,3'-dithiodipropionamide of formula (A-2), which is then subjected to a chlorination/cyclization reaction using a halogenating agent, e.g., chlorine to obtain the desired mixture of the compounds (I) and (II).

The reaction sequence shown in Reaction Scheme 1 generates, however, a significant amount of the compound of formula (III) which is a well-known, potent skin irritant. Further, the result of an animal test has also shown that the skin exposed to the dichloro compound of formula (III) becomes sensitized, i.e., the exposed skin becomes further irritated by the action of the 5-chloro compound of formula (II) (see Bruze et al., Dermatosen 5, 165–168 (1987)).

Meanwhile, U.S. Pat. No. 5,068,338 describes N-methyl-3-(N-methylamino)-aminopropionamide of formula (F) as one of the impurities generated via Reaction Scheme 2 during the preparation of the mixture of the compounds (I) and (II):

Reaction Scheme 2

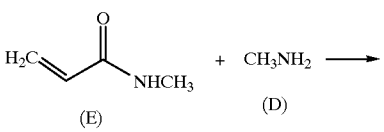

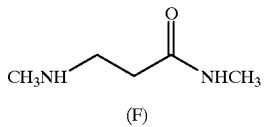

(F)

In this Scheme, N-methylacrylamide of formula (E), which is formed by the decomposition of the compound of formula (A-2), undergoes a 1,4-adduction reaction with methylamine of formula (D), producing N-methyl-3-(N-methylamino)aminopropion-amide (F). The compound of formula (F) is a nitrosamine precursor, and it may further react with N-methylacrylamide (E) to produce another nitroamine precursor.

The U.S. Pat. No. 5,068,338 also discloses that the nitrosamine precursor of formula (F) may subsequently convert to N-methyl-3-(N-nitroso)aminopropionamide (B), a suspected carcinogen, by the action of a metal nitrate ($NO_x$) which is a stabilizer added in formulating an isothiazolone composition, as shown in Reaction Scheme 3:

Reaction Scheme 3

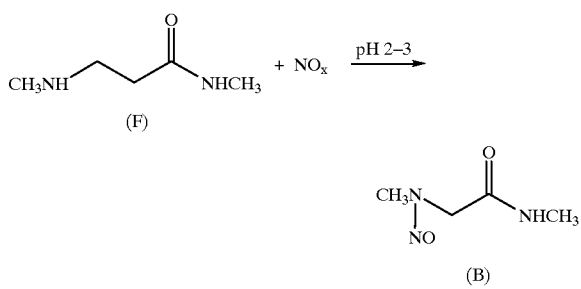

In accordance with Examples of the above-cited patent, the nitrosamine precursor is present in an amount ranging from 0.5% (5,000 ppm) to 1.1% (11,000 ppm) in N,N'-dimethyl-3,3'- dithiodipropionamide of formula (A-2) after the amidation, and the nitrosamine is present in an amount ranging from 750 to 1650 ppm in 15% isothiazolone composition.

Many efforts have been, therefore, made to prepare a mixture of the compounds (I) and (II) which is substantially free of the nitrosamine precursor. For instance, U.S. Pat. Nos. 4,939,266, 5,068,338 and 5,312,827 disclose processes for controlling the amount of the nitrosamine and nitrosamine precursor produced during the preparation of the mixture of the compounds (I) and (II) to a range of 100 ppm or less by using separation techniques such as ion exchange, recrystallization and solvent extraction, or by using a nucleophilic scavenger of N-methylacrylamide (E), as shown in Reaction Scheme 4:

Reaction Scheme 4

(i) Ion Exchange Method:

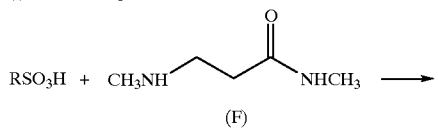

(ii) Scavenger Method:

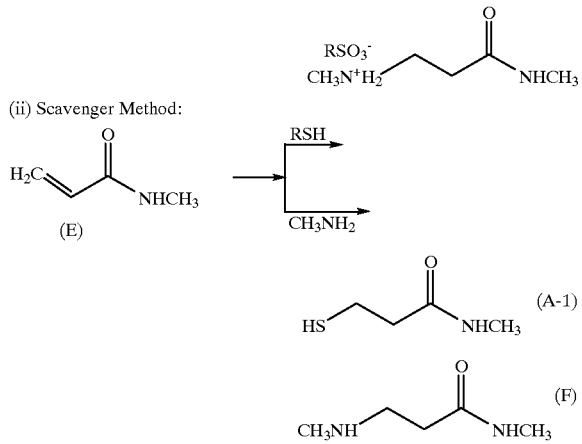

However, these methods have many disadvantages. That is, the ion exchange, recrystallization and solvent extraction methods have the problems of low product yields and long process cycle time. Further, in case of the scavenger method, the production of N-methyl-3-N-nitroso)aminopropionamide of formula (B) may be controlled by reacting N-methyl-3-mercaptopropionamide of formula (A-1) with chlorine gas in an organic solvent. However, a process based on this scavenger method tends to generate an increased amount of the dichloro compound impurity of formula (III), because N-methyl-3- mercaptopropionamide of formula (A-1) reacts with chlorine, generating more heat than N,N'-dimethyl-3,3'-dithiopropionamide of formula (A-2) does.

Accordingly, the methods disclosed in the above patents have severe limitations when the mixture of the compounds (I) and (II) is to be used in products such as cosmetics and medicines, i.e., they have problems in terms of the production time, product yield and, in particular, toxicity of the impurities present in the product.

The present inventors have endeavored to develop a process for preparing a mixture of the compounds (I) and (II) which is substantially free of impurities. As a result, the presence of harmful 4,5-dichloro-2-methyl-4-isothiazolin-3-one (III) in the mixture was defined and it has been found that the compound (III) present in the mixture can be controlled by maintaining the reaction temperature at a range of 5 to 20° C., by way of using a mixed solvent system to internally dissipate the heat of reaction, which may be combined with an optional means for external cooling.

SUMMARY OF THE INVENTION

Accordingly, it is a primary object of the present invention to provide a process for preparing a mixture of 2-methyl-4-isothiazolin-3-one and 5-chloro-2-methyl-4-isothiazolin-3-one as an active ingredient, which is substantially free of 4,5-dichloro-2-methyl-4-isothiazolin-3-one impurity.

It is another object of the present invention to provide a stabilized isothiazolone composition comprising said mixture.

In accordance with one aspect of the present invention, there is provided a process for preparing a mixture of 2-methyl-4-isothiazolin-3-one of formula (I) and 5-chloro-2-methyl-4-isothiazolin-3-one of formula (II) which comprises reacting N-methyl-3-mercaptopropionamide of formula (II) or N,N'-dimethyl-3,3'-dithiodipropionamide of formula (A-2) or a mixture thereof dissolved in a first organic solvent with a chlorinating agent dissolved in a second organic solvent which is different from the first organic solvent, while maintaining the reaction temperature in the range of 5 to 20° C. to obtain said mixture substantially free of 4,5-dichloro-2-methyl-4-isothiazolin-3-one of formula (III):

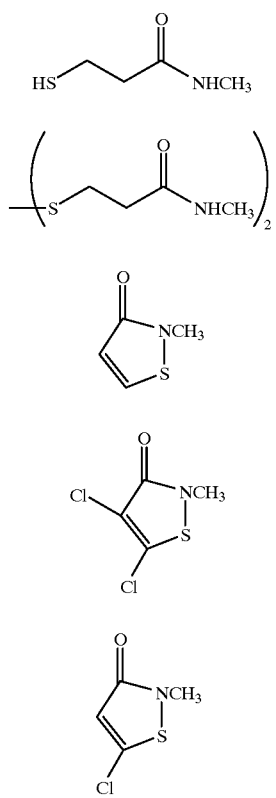

In accordance with a further aspect of the present invention, there is provided a process for preparing a mixture of 2-methyl-4-isothiazolin-3-one (I) and 5-chloro-2-methyl-4-isothiazolin-3-one (II) which further comprises centrifuging the mixture of the compounds (I) and (II) obtained by the chlorination step to obtain the mixture containing nitrosamine or nitrosamine precursors in an amount of less than 5 ppm.

In accordance with another aspect of the present invention, there is provided a stabilized isothiazolone aqueous solution: which comprises water and (A) a biologically effective amount of a mixture of 2-methyl-4-isothiazolin-3-one (I) and 5-chloro-2-methyl-4-isothiazolin-3-one (II) which is prepared by the inventive process; and (B) an effective amount of water soluble metal nitrate stabilizer, said solution being substantially free of 4,5-dichloro-2-methyl-4-isothiazolin-3-one (III).

In accordance with a further aspect of the present invention, there is provided a stabilized isothiazolone composition which comprises: (A) a biologically effective amount of a mixture of 2-methyl-4-isothiazolin-3-one (I) and 5-chloro-2-methyl-4-isothiazolin-3-one (II) which is prepared by the inventive process; (B) an effective amount of a metal nitrate stabilizer; and (C) a sufficient amount of water to dissolve the (A) and (B) components, said composition being substantially free of 4,5-dichloro-2-methyl-4-isothiazolin-3-one (III).

DETAILED DESCRIPTION OF THE INVENTION

The present inventors have found that commercially available isothiazolone compositions contain 4,5-dichloro-2-methyl-4-isothiazolin-3-one (III), which is one of the by-products generated during the preparation of the mixture of the compounds (I) and (II), together with nitrosamine or nitrosamine precursors. The compound (III) should not be present in the composition considering its harmful effect on human even at a trace level.

While nitrosamine or nitrosamine precursor impurities are produced mainly because the disulfide compound of formula (A-2) is used as the starting material, the 4,5-dichloro-2-methyl-4-isothiazolin-3-one (III) is generated as a by-product depending on the reaction temperature, the amount of chlorinating agent employed, the solvent employed and the like in the production of the isothiazolone mixture. In other words, the compound (III) is generated due to excess heat caused by overreaction, or an excess amount of chlorinating agent, etc. in the chlorination and cyclization process.

The present inventors have found for the first time that the compound (III), a known skin irritant, is generated as a by-product in the production of the isothiazolone mixture and that the generation of the compound (III) can be suppressed by controlling the reaction temperature, the amount of chlorinating agent and the solvent composition at a specified range.

In accordance with the present invention, N-methyl-3-mercaptopropionamide of formula (A-1) or N,N'-dimethyl-3,3'-dithiodipropionamide of formula (A-2) or a mixture thereof is employed as the starting material.

The chlorination reaction of the compound (A-1) or (A-2) is strongly exothermic and the heat generated, if not properly controlled, may cause overreaction of the reactants, generating the compound (III) as a by-product in addition to the desired compounds (I) and (II). In the present invention, therefore, the temperature in the reaction system is maintained at a range of 5 to 20° C. to prevent over-chlorination, thereby suppressing the generation of the compound (III).

In general, the heat generated in an exothermic reaction is removed by using an external cooling means of the reaction system. However, this method has a disadvantage in that the reaction heat may be temporarily retained in the reaction system before being transferred out of the reaction system. Accordingly, it is preferred that the reaction heat be removed immediately within the reaction system in order to effectively prevent the overreaction, i.e., it is preferred to use a reaction system wherein the temperature is controlled spontaneously by an internal means.

In the present invention, the control of the reaction temperature is preferably achieved through the use of a mixed solvent system. In one embodiment of the mixed solvent system of the present invention, the starting materials and the chlorinating agent are dissolved in different solvents respectively to stabilize the reactivity of the reactants and, simultaneously, to control the heat of the chlorination reaction, thus enabling the desired reaction to progress without overreaction. Preferably, the mixed solvent system is employed in combination with a means for external cooling, e.g., a water jacket, ice-water bath and acetone-dry ice bath.

Further, in accordance with the present invention, the control of the reaction temperature may also be achieved by using an external cooling means alone when a conventional single solvent system is employed. When the reaction temperature is maintained at a range of 5 to 20° C. by way of using the mixed solvent system or the external cooling means as mentioned above, the chlorination of the reactant proceeds smoothly while suppressing the generation of the compound (III).

If the reaction temperature is below 5° C., the reaction rate is excessively low, and the reaction leads to a biologically ineffective mixture comprising a major portion of 2-methyl-4-isothiazolin-3-one of formula (I) and a minor portion of 5-chloro-2-methyl-4-isothiazolin-3-one of formula (II). When the reaction temperature exceed 20° C., on the other hand, a large amount of 4,5-dichloro-2-methyl-4-isothiazolin-3-one (III) is produced as a by-product. Therefore, when the reaction temperature is maintained at a range of 5 to 20° C., a biologically effective mixture of the compounds (I) and (II) containing little harmful impurities is obtained in a yield of higher than 95 mol %.

In accordance with the present invention, the mixture obtained after the completion of the chlorination at a controlled reaction temperature may be preferably centrifuged to remove impurities such as nitrosamine precursors and nitrosamine still remaining in the product mixture. In the centrifuging step, the loss of the desired mixture of the compounds (I) and (II) is negligibly slight, while other impurities present in the mixture may also be removed in the step.

As previously described, in accordance with the present invention, the generation of 4,5-dichloro-2-methyl-4-isothiazolin-3-one (III) by-product can be effectively suppressed by using a mixed solvent system. The use of the mixed solvent system is advantageous based on the fact that the preparation of the compound (III) requires a larger amount of reaction heat and production heat than that required by the mixture of the compounds (I) and (II).

The mixed solvent system of the present invention is employed as shown in Reaction Scheme 5:

Reaction Scheme 5

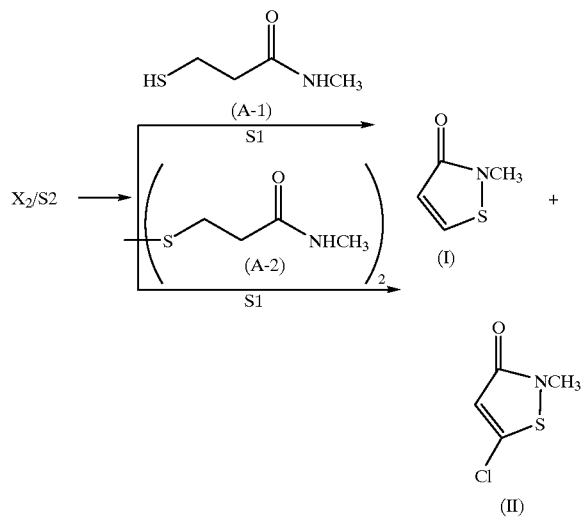

wherein, $X_2$ is $Cl_2$ or $SO_2Cl_2$,

S1 represents a first organic solvent and

S2 represents a second organic solvent.

That is, the compound of formula (A-1) or (A-2), or a mixture thereof is dissolved in a first organic solvent and a chlorinating agent is dissolved in a second organic solvent.

The first organic solvent which may be employed in the mixed solvent system of the present invention include those capable of dissolving the compound of formula (A-1) and/or the compound of formula (A-2) and, at the same time, having larger heat capacity to dissipate largely the reaction heat in the solvent system. Representatives of the first organic solvent include $C_{4-12}$ alkylesters, $C_{7-14}$ hydrocarbons, XCH=CHX, $CH_2$=$CX_2$, $CX_2$=$CX_2$, CHX=$CX_2$, $C_{8-12}$ aromatic hydrocarbons and $C_6H_{(6-n)}X_n$ wherein n is an integer of 1 to 5 and X represents a halogen atom. The compounds (A-1) and/or (A-2) and the first organic solvent are generally mixed in a weight ratio of 1:0.2 to 1:20. If the first organic solvent is employed in an amount of less than the lower limit, it is not sufficient to dissolve the starting material, and if the amount of the first organic solvent exceeds the upper limit, it is not economical.

The chlorinating agent which may be used in the present invention is sulfuryl chloride ($SO_2Cl_2$) or chlorine gas ($Cl_2$), preferably sulfuryl chloride. The temperature of the chlorination reaction may depend on the solvents selected. The larger the heat capacity of the solvent is, the easier the control of the temperature of the reaction system is. The solvents having large heat capacity are meant to be those having large heat of vaporization.

In the mixed solvent system of the present invention, the second organic solvent for the chlorinating agent may include those capable of dissolving the chlorinating agent and generating not so much mixing heat when mixed with the organic solvent. The chlorinating agent solution is stirred for 10 to 60 minutes. Representatives of the second solvent include $C_{2-10}$ alkylethers, $C_{2-8}$ alkylesters, $C_{5-12}$ aromatic hydrocarbons, $CH_2X_2$, $CHCX_3$, $CX_4$, $CH_3CX_3$, $CH_2XCH_2X$ (wherein X represents a halogen atom) and $C_{6-10}$ aromatic hydrocarbons. The chlorinating agent and the second organic solvent are mixed in a weight ratio of 1:1 to 1:20. If the second organic solvent is employed in an amount of less than the lower limit, it is not sufficient to dissolve the chlorinating agent so that a shock caused by the reaction heat cannot be alleviated, and if the amount of the second organic solvent exceeds the upper limit, it is not economical.

The specific combination of the first and the second solvents enhances the effect of the mixed solvent system of the present invention. In the preferred embodiment, the first and the second solvents are employed in a combination of $C_6H_{(6-n)}X_n$ and a $C_{4-6}$ alkylester, of $C_2H_nX_{(4-n)}$ and $CHX_nX_{4-n}$, and of a $C_{4-6}$ alkylester and a $C_{6-10}$ aromatic hydrocarbon, respectively, wherein X is a halogen atom and n is an integer of 1 to 5. In the present invention, the compounds (I) and (II) used as starting material and the chlorinating agent are employed in a molar ratio of 1:2 to 1:10. The organic solvents employed in the chlorination step may be recycled into the reaction system without an additional separation step, thus lowering the production cost.

The compound (I) and the compound (II) in the isothiazolone mixture obtained in accordance with the process of the present invention are preferably present in a molar ratio of 1:3 to 1:10.

The amount of the mixture of the compounds (I) and (II) used as the active ingredient in the composition of the present invention generally ranges from 1.5 to 15% by weight of the composition of the present invention, although it may be varied depending on the final use of the composition.

Representatives of the metal nitrate stabilizer which may be used in the composition include water soluble metal nitrates such as sodium nitrate, potassium nitrate, calcium nitrate, magnesium nitrate, copper nitrate, ferric nitrate, ferrous nitrate, nickel nitrate, zinc nitrate, barium nitrate, manganese nitrate, cobalt nitrate and a mixture thereof. The stabilizer is generally employed in an amount ranging from 1 to 30% by weight, preferably from 2 to 20% by weight of the composition.

The present invention also comprises, within its scope, a stabilized isothiazolone composition or solution which comprises a biologically effective amount of a mixture of the compounds (I) and (II) prepared by the inventive process as described previously, an effective amount of a metal nitrate stabilizer and a sufficient amount of water to dissolve the above two components, said composition being substantially free of both 4,5-dichloro-2-methyl-4-isothiazolin-3-one (III) and nitrosamine or its precursors.

Further, the present invention comprises within its scope a stabilized isothiazolone composition or solution comprising a biologically effective amount of a mixture of the compounds (I) and (II) prepared by the inventive process as described previously, said composition containing less than 100 ppm of 4,5-dichloro-2-methyl-4-isothiazolin-3-one (III) and less than 5 ppm of nitrosamine or its precursors.

Commercially available isothiazolone compositions or solutions, and those disclosed in U.S. Pat. Nos. 4,939,266, 5,068,338, and 5,312,827 typically contain nitrosamine or its precursors in an amount of at least 100 ppm in 15% composition or solution. Whereas, in the isothiazolone compositions or solutions prepared in accordance with the present invention, the biologically effective mixture comprising the compounds (I) and (II) contain no or less than 5 ppm of nitrosamine or its precursors by simply centrifuging the mixture obtained after the chlorination.

Although the above mentioned U.S. Patents do not mention the presence of the compound (III) known as a skin-irritant, it is believed that the isothiazolone compositions or solutions disclosed therein will perhaps contain a relatively larger amount of the compound (III) which is generated inevitably in the isothiazolone mixture preparation process according to the prior methods. In contrast, the isothiazolone composition or solution prepared by the inventive process is substantially free of or less than 100 ppm of the compound (III) by way of controlling the reaction temperature strictly.

The following Examples are given for the purpose of illustration only and are not intended to limit the scope of the invention. All units, percentages, parts, etc. as used in the Examples are by weight, unless otherwise specified.

In Examples, HPLC (high performance liquid chromatography) analysis of the samples was conducted under the following conditions:

Column: $\mu$-Bondapak C18 (3.9×300 mm)

Mobile Phase: Methanol/water=2/3

Flow rate: 1.0 ml/min.

Temperature: 25° C.

EXAMPLE 1

A one-liter three-necked round-bottled flask equipped with a thermometer, a dropping funnel and a stirrer was charged with 310 g of diethyl ether and 72 g (0.53 mol) of sulfuryl chloride ($SO_2Cl_2$) at 0° C. Thereto, a solution of 30 g (0.25 mol) of N-methyl-3-mercaptopropionamide (purity 99%) in 120 g of 1,2-dichloroethylene, previously cooled to −5° C., was slowly added over 2 hours, and the mixture was stirred at a reaction temperature of 5° C. for 2 hours and then allowed to stand for 1 hour. Subsequently, the solution was centrifuged to obtain 42.2 g (yield 83%) of the product mixture containing 2-methyl-4-isothiazolin-3-one of formula (I) and 5-chloro-2-methyl-4-isothiazolin-3-one of formula (II) as white colored crystals, which were analyzed by HPLC and the results are shown in Table 1.

EXAMPLE 2

A one-liter three-necked round-bottled flask equipped with a thermometer, a dropping funnel and a stirrer was charged with 360 g of n-hexane and 76 g (0.56 mol) of sulfuryl chloride at −5° C. Thereto, a solution of 30 g (0.25 mol) of N-methyl-3-mercaptopropionamide in 160 g of n-hexyl acetate, maintained at 10° C., was slowly added over 2 hours, and the mixture was stirred at a reaction temperature of 11° C. for 2 hours and then allowed to stand for 1 hour. Subsequently, the resulting solution was centrifuged to obtain 47.4 g (yield 98%) of the product mixture as white colored crystals, which were analyzed by HPLC and the results are shown in Table 1.

EXAMPLE 3

A 300 ml three-necked round-bottled flask equipped with a thermometer, a dropping funnel and a stirrer was charged with 78 g of chloroform and 76 g (0.56 mol) of sulfuryl chloride at −5° C. Thereto, a solution of 30 g (0.25 mol) of N-methyl-3-mercaptopropionamide in 6 g of tetrachloroethylene, maintained at 10° C., was slowly added over 2 hours, and the mixture was stirred at a reaction temperature of 14° C. for 2 hours and then allowed to stand for 1 hour. Subsequently, the solution was centrifuged to obtain 43.6 g (yield 89%) of the product mixture as white colored crystals, which were analyzed by HPLC and the results are shown in Table 1.

EXAMPLE 4

A three-liter three-necked round-bottled flask equipped with a thermometer, a dropping funnel and a stirrer was charged with 1500 g of toluene and 76 g (0.56 mol) of sulfuryl chloride at −5° C. Thereto, a solution of 30 g (0.25 mol) of N-methyl-3-mercaptopropionamide in 300 g of n-decane, maintained at 10° C., was slowly added over 2 hours, and the mixture was stirred at a reaction temperature of 13° C. for 2 hours and then allowed to stand for 1 hour. Subsequently, the solution was centrifuged to obtain 46.2 g (yield 98%) of the product mixture as white colored crystals, which were analyzed by HPLC and the results are shown in Table 1.

EXAMPLE 5

A one-liter three-necked round-bottled flask equipped with a thermometer, a dropping funnel and a stirrer was charged with 440 g of n-propyl acetate and 82 g (0.61 mol) of sulfuryl chloride at −5° C. Thereto, a solution of 30 g (0.25 mol) of N-methyl-3-mercaptopropionamide in 140 g of p-xylene, maintained at 10° C, was slowly added over 2 hours, and the mixture was stirred at a reaction temperature of 12° C. for 2 hours and then allowed to stand for 1 hour. Subsequently, the solution was centrifuged to obtain 46.2 g (yield 98%) of the product mixture as white colored crystals, which were analyzed by HPLC and the results are shown in Table 1.

EXAMPLE 6

A one-liter three-necked round-bottled flask equipped with a thermometer, a dropping funnel and a stirrer was charged with 380 g of dichloromethane and 70 g (0.52 mol) of sulfuryl chloride at −5° C. Thereto, a solution of 30 g (0.25 mol) of N-methyl-3-mercaptopropionamide in 10 g of 1,1,2-trichloroethane, maintained at 10° C., was slowly added over 2 hours, and the mixture was stirred at a reaction temperature of 16° C. for 2 hours and then allowed to stand for 1 hour. Subsequently, the solution was centrifuged to obtain 46.2 g (yield 98%) of the product mixture as white colored crystals, which were analyzed by HPLC and the results are shown in Table 1.

EXAMPLE 7

A three-liter three-necked round-bottled flask equipped with a thermometer, a dropping funnel and a stirrer was charged with 1100 g of 1,2-dichloroethane and 76 g (0.56 mol) of sulfuryl chloride at −5° C. Thereto, a solution of 30 g (0.25 mol) of N-methyl-3-mercaptopropionamide in 600 g of monochlorobenzene, maintained at 10° C., was slowly added over 2 hours, and the mixture was stirred at a reaction temperature of 14° C. for 2 hours and then allowed to stand for 1 hour. Subsequently, the solution was centrifuged to obtain 46.2 g (yield 98%) of the product mixture as white colored crystals, which were analyzed by HPLC and the results are shown in Table 1.

EXAMPLE 8

A three-liter three-necked round-bottled flask equipped with a thermometer, a dropping funnel and a stirrer was charged with 1000 g of toluene and 76 g (0.56 mol) of sulfuryl chloride at −5° C. Thereto, a solution of 30 g (0.25 mol) of N-methyl-3-mercaptopropionamide in 180 g of ethyl acetate, maintained at 10° C., was slowly added over 2 hours, and the mixture was stirred at a reaction temperature of 13° C. for 2 hours and then allowed to stand for 1 hour. Subsequently, the solution was centrifuged to obtain 45.9 g (yield 98%) of the product mixture as white colored crystals, which were analyzed by HPLC and the results are shown in Table 1.

EXAMPLE 9

A three-liter three-necked round-bottled flask equipped with a thermometer, a dropping funnel and a stirrer was charged with 1380 g of ethyl acetate and 76 g (0.56 mol) of sulfuryl chloride at −5° C. Thereto, a solution of 30 g (0.25 mol) of N-methyl-3-mercaptopropionamide in 10 g of toluene, maintained at 10° C., was slowly added over 2 hours, and the mixture was stirred at a reaction temperature of 12° C. for 2 hours and then allowed to stand for 1 hour. Subsequently, the solution was centrifuged to obtain 46.2 g (yield 98%) of the product mixture as white colored crystals, which were analyzed by HPLC and the results are shown in Table 1.

EXAMPLE 10

A two-liter three-necked round-bottled flask equipped with a thermometer, a dropping funnel and a stirrer was charged with 1100 g of butyl acetate and 76 g (0.56 mol) of sulfuryl chloride at −5° C. Thereto, a solution of 30 g (0.25 mol) of N-methyl-3-mercaptopropionamide in 15 g of monochlorobenzene, maintained at 10° C., was slowly added over 2 hours, and the mixture was stirred at a reaction temperature of 15° C. for 2 hours and then allowed to stand for 1 hour. Subsequently, the solution was centrifuged to obtain 46.4 g (yield 98%) of the product mixture as white colored crystals, which were analyzed by HPLC and the results are shown in Table 1.

EXAMPLE 11

A two-liter three-necked round-bottled flask equipped with a thermometer, a dropping funnel and a stirrer was charged with 1000 g of butyl acetate and 76 g (0.56 mol) of sulfuryl chloride at −5° C. Thereto, a solution of 30 g (0.25 mol) of N-methyl-3-mercaptopropionamide in 12 g of 1,2-dichlorobenzene, maintained at 10° C., was slowly added over 2 hours, and the mixture was stirred at a reaction temperature of 14° C. for 2 hours and then allowed to stand for 1 hour. Subsequently, the solution was centrifuged to obtain 46.3 g (yield 98%) of the product mixture as white colored crystals, which were analyzed by HPLC and the results are shown in Table 1.

EXAMPLE 12

A 300 ml three-necked round-bottled flask equipped with a thermometer, a dropping funnel and a stirrer was charged with 72 g of diethylether and 72 g (0.53 mol) of sulfuryl chloride at 0° C. Thereto, a solution of 24 g (0.10 mol) of N,N'-dimethyl-3,3'-dithiodipropionamide (purity 99%) in 5 g of 1,2-dichloro-ethylene, previously cooled to −5° C., was slowly added over 2 hours, and the mixture was stirred at a reaction temperature of 6° C. for 2 hours and then allowed to stand for 1 hour. Subsequently, the solution was centrifuged to obtain 42.2 g (yield 83%) of the product mixture as white colored crystals, which were analyzed by HPLC and the results are shown in Table 1.

EXAMPLE 13

A one-liter three-necked round-bottled flask equipped with a thermometer, a dropping funnel and a stirrer was charged with 300 g of n-hexane and 76 g (0.56 mol) of sulfuryl chloride at −5° C. Thereto, a solution of 24 g (0.10 mol) of N,N'-dimethyl-3,3'-dithiodipropionamide in 160 g of n-hexyl acetate, maintained at 10° C., was slowly added over 2 hours, and the mixture was stirred at a reaction temperature of 8° C. for 2 hours and then allowed to stand for 1 hour.

Subsequently, the solution was centrifuged to obtain 47.4 g (yield 98%) of the product mixture as white colored crystals, which were analyzed by HPLC and the results are shown in Table 1.

EXAMPLE 14

A 500 ml three-necked round-bottled flask equipped with a thermometer, a dropping funnel and a stirrer was charged with 200 g of chloroform and 76 g (0.56 mol) of sulfuryl chloride at −5° C. Thereto, a solution of 24 g (0.10 mol) of N,N'-dimethyl-3,3'-dithiodipropionamide in 60 g of tetrachloroethylene, maintained at 10° C., was slowly added over 2 hours, and the mixture was stirred at a reaction temperature of 19° C. for 2 hours and then allowed to stand for 1 hour. Subsequently, the solution was centrifuged to obtain 43.6 g (yield 89%) of the product mixture as white colored crystals, which were analyzed by HPLC and the results are shown in Table 1.

EXAMPLE 15

A two-liter three-necked round-bottled flask equipped with a thermometer, a dropping funnel and a stirrer was charged with 980 g of toluene and 76 g (0.56 mol) of sulfuryl chloride at −5° C. Thereto, a solution of 24 g (0.10 mol) of N,N'-dimethyl-3,3'-dithiodipropionamide in 24 g of n-decane, maintained at 10° C., was slowly added over 2 hours, and the mixture was stirred at a reaction temperature of 17° C. for 2 hours and then allowed to stand for 1 hour. Subsequently, the solution was centrifuged to obtain 46.2 g (yield 98%) of the product mixture as white colored crystals, which were analyzed by HPLC and the results are shown in Table 1.

EXAMPLE 16

A one-liter three-necked round-bottled flask equipped with a thermometer, a dropping funnel and a stirrer was charged with 380 g of n-propyl acetate and 76 g (0.56 mol) of sulfuryl chloride at −5° C. Thereto, a solution of 24 g (0.10 mol) of N,N'-dimethyl-3,3'-dithiodipropionamide in 150 g of p-xylene, maintained at 10° C., was slowly added over 2 hours, and the mixture was stirred at a reaction temperature of 14° C. for 2 hours and then allowed to stand for 1 hour. Subsequently, the solution was centrifuged to obtain 46.2 g (yield 98%) of the product mixture as white colored crystals, which were analyzed by HPLC and the results are shown in Table 1.

EXAMPLE 17

A two-liter three-necked round-bottled flask equipped with a thermometer, a dropping funnel and a stirrer was charged with 1110 g of dichloromethane and 76 g (0.56 mol) of sulfuryl chloride at −5° C. Thereto, a solution of 24 g (0.10 mol) of N,N'-dimethyl-3,3'-dithiodipropionamide in 15 g of 1,1,2-trichloroethane, maintained at 10° C., was slowly added over 2 hours, and the mixture was stirred at a reaction temperature of 15° C. for 2 hours and then allowed to stand for 1 hour. Subsequently, the solution was centrifuged to obtain 46.2 g (yield 98%) of the product mixture as white colored crystals, which were analyzed by HPLC and the results are shown in Table 1.

EXAMPLE 18

A one-liter three-necked round-bottled flask equipped with a thermometer, a dropping funnel and a stirrer was charged with 480 g of 1,2-dichloroethane and 76 g (0.56 mol) of sulfuryl chloride at −5° C. Thereto, a solution of 24 g (0.10 mol) of N,N'-dimethyl-3,3'-dithiodipropionamide in 50 g of monochlorobenzene, maintained at 10° C., was slowly added over 2 hours, and the mixture was stirred at a reaction temperature of 16° C. for 2 hours and then allowed to stand for 1 hour. Subsequently, the solution was centrifuged to obtain 46.2 g (yield 98%) of the product mixture as white colored crystals, which were analyzed by HPLC and the results are shown in Table 1.

EXAMPLE 19

A two-liter three-necked round-bottled flask equipped with a thermometer, a dropping funnel and a stirrer was charged with 980 g of toluene and 76 g (0.56 mol) of sulfuryl chloride at −5° C. Thereto, a solution of 24 g (0.10 mol) of N,N'-dimethyl-3,3'-dithiodipropionamide in 7 g of ethyl acetate, maintained at 10° C., was slowly added over 2 hours, and the mixture was stirred at a reaction temperature of 14° C. for 2 hours and then allowed to stand for 1 hour. Subsequently, the solution was centrifuged to obtain 46.0 g (yield 98%) of the product mixture as white colored crystals, which were analyzed by HPLC and the results are shown in Table 1.

EXAMPLE 20

A two-liter three-necked round-bottled flask equipped with a thermometer, a dropping funnel and a stirrer was charged with 1000 g of ethyl acetate and 76 g (0.56 mol) of sulfuryl chloride at −5° C. Thereto, a solution of 24 g (0.10 mol) of N,N'-dimethyl-3,3'-dithiodipropionamide in 32 g of toluene, maintained at 10° C., was slowly added over 2 hours, and the mixture was stirred at a reaction temperature of 5° C. for 2 hours and then allowed to stand for 1 hour. Subsequently, the solution was centrifuged to obtain 47.4 g (yield 98%) of the product mixture as white colored crystals, which were analyzed by HPLC and the results are shown in Table 1.

EXAMPLE 21

A one-liter three-necked round-bottled flask equipped with a thermometer, a dropping funnel and a stirrer was charged with 580 g of butyl acetate and 76 g (0.56 mol) of sulfuryl chloride at −5° C. Thereto, a solution of 24 g (0.10 mol) of N,N'-dimethyl-3,3'-dithiodipropionamide in 10 g of monochlorobenzene, maintained at 10° C., was slowly added over 2 hours, and the mixture was stirred at a reaction temperature of 11° C. for 2 hours and then allowed to stand for 1 hour. Subsequently, the solution was centrifuged to obtain 46.2 g (yield 98%) of the product mixture as white colored crystals, which were analyzed by HPLC and the results are shown in Table 1.

EXAMPLE 22

A two-liter three-necked round-bottled flask equipped with a thermometer, a dropping funnel and a stirrer was charged with 800 g of butyl acetate and 76 g (0.56 mol) of sulfuryl chloride at −5° C. Thereto, a solution of 24 g (0.10 mol) of N,N'-dimethyl-3,3'-dithiodipropionamide in 8 g of 1,2-dichlorobenzene, maintained at 10° C., was slowly added over 2 hours, and the mixture was stirred at a reaction temperature of 15° C. for 2 hours and then allowed to stand for 1 hour. Subsequently, the solution was centrifuged to obtain 45.9 g (yield 98%) of the product mixture as white colored crystals, which were analyzed by HPLC and the results are shown in Table 1.

Comparative Example 1

A one liter three-necked round-bottled flask equipped with a thermometer, a dropping funnel and a stirrer was charged with 500 g of ethyl acetate and, thereto, 21.3 g (0.3 mol) of chlorine gas ($Cl_2$) was introduced at 15° C. Then, 11.9 g (0.10 mol) of N-methyl-3-mercaptopropionamide was added in divided ten portions to the reaction mixture. The reaction temperature in the flask was 35° C. The reaction solution was filtered with a Buchner funnel to collect precipitates, which were washed with ethyl acetate and dried to obtain 13.5 g (yield 62%) of the product mixture as white colored crystals, which were analyzed by HPLC and the results are shown in Table 1.

Comparative Example 2

A three-liter three-necked round-bottled flask equipped with a thermometer, a dropping funnel and a stirrer was charged with 1280 g of butyl acetate and 76 g (0.56 mol) of sulfuryl chloride at −35° C. Thereto, a solution of 20 g (0.17 mol) of N-methyl-3-mercaptopropionamide in 10 g of butyl acetate, maintained at 0° C., was slowly added over 8 hours, and the mixture was stirred at a reaction temperature of 25° C. for 8 hours and then allowed to stand for 1 hour. Subsequently, the solution was centrifuged to obtain 38.2 g (yield 78%) of the product mixture as white colored crystals, which were analyzed by HPLC and the results are shown in Table 1.

Comparative Example 3

A three-liter three-necked round-bottled flask equipped with a thermometer, a dropping funnel and a stirrer was charged with 1380 g of benzene and 76 g (0.56 mol) of sulfuryl chloride at 5° C. Thereto, a solution of 30 g (0.25 mol) of N-methyl-3-mercaptopropionamide in 10 g of benzene, maintained at 15° C., was slowly added over 2 hours, and the mixture was stirred at a reaction temperature of 20° C. for 2 hours and then allowed to stand for 1 hour, to obtain 46.2 g (yield 98%) of the product mixture as white colored crystals, which were analyzed by HPLC and the results are shown in Table 1.

Comparative Example 4

A two-liter three-necked round-bottled flask equipped with a thermometer, a dropping funnel and a stirrer was charged with 1000 g of xylene and 76 g (0.56 mol) of sulfuryl chloride at 5° C. Thereto, a solution of 30 g (0.25 mol) of N-methyl-3-mercaptopropionamide in 12 g of xylene, maintained at 14° C. was slowly added over 2 hours, and the mixture was stirred at a reaction temperature of 19° C. for 2 hours and then allowed to stand for 1 hour, to obtain 46.3 g (yield 98%) of the product mixture as white colored crystals, which were analyzed by HPLC and the results are shown in Table 1.

Comparative Example 5

A two-liter three-necked round-bottled flask equipped with a thermometer, a dropping funnel and a stirrer was charged with 1000 g of toluene and 76 g (0.56 mol) of sulfuryl chloride at 5° C. Thereto, 24 g (0.10 mol) of N,N'-dimethyl-3,3'-dithiodipropionamide was slowly added over 2 hours, and the resulting mixture was stirred at a reaction temperature of 19° C. for 2 hours and then allowed to stand for 1 hour, to obtain 46.2 g (yield 98%) of the product mixture as white colored crystals, which were analyzed by HPLC and the results are shown in Table 1.

Comparative Example 6

A one-liter three-necked round-bottled flask equipped with a thermometer, a dropping funnel and a stirrer was charged with 200 g of benzene and 24 g (0.10 mol) of N,N'-dimethyl-3,3'-dithiodipropionamide at 5° C. Thereto, 76 g (0.56 mol) of sulfuryl chloride was slowly added over 4 hours, and the resulting mixture was stirred at a reaction temperature of 6° C. for 2 hours and then allowed to stand for 1 hour, to obtain 45.2 g of the product mixture as white colored crystals, which were analyzed by HPLC and the results are shown in Table 1.

Comparative Example 7

A one-liter three-necked round-bottled flask equipped with a thermometer, a dropping funnel and a stirrer was charged with 180 g of benzene and 24 g (0.10 mol) of N,N'-dimethyl-3,3'-dithiodipropionamide at 5° C. Thereto, 76 g (0.56 mol) of sulfuryl chloride dissolved in 20 g of benzene was slowly added over 4 hours, and the resulting mixture was stirred at a reaction temperature of 6° C. for 2 hours and then allowed to stand for 1 hour, to obtain 45.2 g of the product mixture as white colored crystals, which were analyzed by HPLC and the results are shown in Table 1.

TABLE 1

| | Compound (I) (%) | Compound (II) (%) | Compound (III) (ppm) | HCl (%) | Others (%) |
|---|---|---|---|---|---|
| Ex. 1 | 16.0 | 52.0 | 30 | 29.7 | 0.27 |
| Ex. 2 | 18.3 | 55.2 | 50 | 26.2 | 0.25 |
| Ex. 3 | 16.3 | 54.1 | 40 | 27.5 | 0.04 |
| Ex. 4 | 18.0 | 54.0 | 50 | 27.7 | 0.23 |
| Ex. 5 | 18.2 | 53.7 | 60 | 27.7 | 0.34 |
| Ex. 6 | 17.0 | 53.6 | 55 | 27.7 | 0.23 |
| Ex. 7 | 16.0 | 52.0 | 49 | 27.7 | 0.23 |
| Ex. 8 | 16.3 | 52.2 | 46 | 27.7 | 0.23 |
| Ex. 9 | 17.9 | 51.8 | 32 | 27.7 | 0.23 |
| Ex. 10 | 16.1 | 52.1 | 24 | 27.7 | 0.23 |
| Ex. 11 | 17.8 | 51.7 | 33 | 27.7 | 0.23 |
| Ex. 12 | 17.6 | 55.2 | 35 | 29.7 | 0.27 |
| Ex. 13 | 18.3 | 55.2 | 51 | 26.2 | 0.25 |
| Ex. 14 | 16.2 | 54.3 | 59 | 27.5 | 0.04 |
| Ex. 15 | 18.5 | 53.8 | 47 | 27.7 | 0.23 |
| Ex. 16 | 18.2 | 53.7 | 43 | 27.7 | 0.34 |
| Ex. 17 | 17.3 | 54.1 | 15 | 27.7 | 0.23 |
| Ex. 18 | 16.3 | 52.3 | 23 | 27.7 | 0.23 |
| Ex. 19 | 16.0 | 52.0 | 21 | 27.7 | 0.23 |
| Ex. 20 | 17.9 | 52.0 | 37 | 27.7 | 0.23 |
| Ex. 21 | 16.0 | 52.3 | 43 | 27.7 | 0.23 |
| Com. Ex. 1 | 24.0 | 41.0 | 33600 | 30.4 | 1.30 |
| Com. Ex. 2 | 25.2 | 42.6 | 11000 | 30.8 | 0.30 |
| Com. Ex. 3 | 17.9 | 51.8 | 420 | 27.7 | 0.23 |
| Com. Ex. 4 | 17.8 | 51.7 | 560 | 27.7 | 0.23 |
| Com. Ex. 5 | 18.5 | 53.8 | 490 | 27.7 | 0.23 |
| Com. Ex. 6 | 25.3 | 44.9 | 410 | 29.8 | 0.22 |
| Com. Ex. 7 | 27.5 | 44.1 | 440 | 28.4 | 0.23 |

Footnote:
Compound (I): 2-methyl-4-isothiazolin-3-one
Compound (II): 5-chloro-2-methyl-4-isothiazolin-3-one
Compound (III): 4,5-dichloro-2-methyl-4-isothiazolin-3-one Comparative Examples 1 to 7 clearly illustrate the advantages of carrying out the reaction at a temperature in the range of 5 to 20° C. with a first organic solvent for the chlorinating agent and a second organic solvent which is different from the first organic solvent in order to obtain the desired mixture containing less than 100 ppm of the undesirable impurity 4,5-dichloro-2-methyl-4-isothiazolin-3-one.

In Comparative Example 1, the chlorination of the reactants was carried out in a solvent (ethyl acetate) with chlorine gas, and the amount of the impurity produced was 33,600 ppm. In Comparative Example 2, the same solvent (butyl acetate) was used for both the chlorinating agent and the reactant, the reaction was carried out at a temperature in the range of −35 to 0° C., and the amount of the impurity produced was 11,000 ppm. In Comparative Examples 3, 4 and 7, the same solvent was used for both the chlorinating agent and the reactant while the reaction was carried out at a temperature within the present invention, and the amount of impurity produced ranged from 420 to 560 ppm. In Comparative Example 5, a solvent was used only for the chlorinating agent and the amount of impurity produced ranged from 490 ppm. In Comparative Example 6, a solvent was used only for the reactant and the amount of impurity produced ranged from 410 ppm.

EXAMPLE 23

Preparation of Stabilized Isothiazolone Compositions

A 250 ml three-necked round-bottled flask equipped with a stirrer and a pH meter was charged with 59.7 g of water and 38 g of Mg(NO$_3$)$_2$6H$_2$O, and the resulting mixture was stirred for 30 minutes. Thereto, 2.1 g of the crystals obtained in one of Examples 1 to 22 and Comparative Examples 1 and 2 was added, and the resultant mixture was stirred for 30 minutes and adjusted to pH 2 to 5 with the addition of MgO.

The compositions thus obtained were analyzed by HPLC and the results are shown in Table 2.

Further, the APHA Color values of the compositions were determined in accordance with ASTM D 1209 in order to quantify any impurities which are capable of developing colors in an aqueous solution, and the results are also shown in Table 2. The higher the value of the APHA color is, the larger the content of the impurities is.

TABLE 2

| Compound Employed | Compound (I)(%) | Compound (II)(%) | Compound (III)(ppm) | Compound (B)(ppm) | $Mg(NO_3)_2$(%) | $MgCl_2$(%) | $H_2O$(%) | APHA Color |
|---|---|---|---|---|---|---|---|---|
| Ex. 4 | 0.38 | 1.13 | 0.75 | 0 | 22 | 0.5 | 76 | 20 |
| Ex. 5 | 0.38 | 1.12 | 0.90 | 0 | 22 | 0.5 | 76 | 30 |
| Ex. 6 | 0.36 | 1.12 | 0.83 | 0 | 22 | 0.5 | 76 | 40 |
| Ex. 7 | 0.34 | 1.09 | 0.74 | 0 | 22 | 0.5 | 76 | 50 |
| Ex. 8 | 0.34 | 1.09 | 0.69 | 0 | 22 | 0.5 | 76 | 10 |
| Ex. 9 | 0.34 | 1.09 | 0.48 | 0 | 22 | 0.5 | 76 | 30 |
| Ex. 10 | 0.34 | 1.09 | 0.36 | 0 | 22 | 0.5 | 76 | 50 |
| Ex. 11 | 0.34 | 1.09 | 0.50 | 0 | 22 | 0.5 | 76 | 30 |
| Ex. 15 | 0.38 | 1.13 | 0.71 | 0 | 22 | 0.5 | 76 | 20 |
| Ex. 16 | 0.38 | 1.12 | 0.64 | 0 | 22 | 0.5 | 76 | 30 |
| Ex. 17 | 0.36 | 1.12 | 0.23 | 0 | 22 | 0.5 | 76 | 40 |
| Ex. 18 | 0.34 | 1.09 | 0.35 | 0 | 22 | 0.5 | 76 | 50 |
| Ex. 19 | 0.34 | 1.09 | 0.32 | 0 | 22 | 0.5 | 76 | 50 |
| Ex. 20 | 0.34 | 1.09 | 0.56 | 0 | 22 | 0.5 | 76 | 50 |
| Ex. 21 | 0.34 | 1.09 | 0.65 | 0 | 22 | 0.5 | 76 | 50 |
| Ex. 22 | 0.34 | 1.09 | 0.47 | 0 | 22 | 0.5 | 76 | 50 |
| Com. Ex. 1 | 0.50 | 0.86 | 50400 | 110 | 22 | 0.5 | 76 | 170 |
| Com. Ex. 2 | 0.24 | 0.80 | 550 | 132 | 22 | 0.5 | 76 | 150 |

Tables 1 and 2 shows that the mixtures of the compounds (I) and (II) prepared in accordance with the present invention comprise the compounds (I) and (II) in a biologically effective molar ratio, i.e., a molar ratio of 1:3 to 10, enabling them to be useful as a biocide in various products. Further, the mixture thus prepared can be safely employed because they contain trace amounts of the compound (III) and nitrosamine impurities and has the APHA Color value of less than 50.

While the invention has been described in connection with the above specific embodiments, it should be recognized that various modifications and changes may be made to the present invention and also fall within the scope of the invention as defined by the claims that follow.

What is claimed is:

1. A process for preparing a mixture of 2-methyl-4-isothiazolin-3-one of formula (I) and 5-chloro-2-methyl-4-isothiazolin-3-one of formula (II) which comprises: reacting N-methyl-3-mercaptopropionamide of formula (A-1) or N,N'-dimethyl-3,3'-dithiodipropionamide of formula (A-2) or a mixture thereof dissolved in a first organic solvent with sulfuryl chloride dissolved in a second organic solvent which is different from the first organic solvent, while maintaining the reaction temperature in the range of 5 to 20° C. to obtain said mixture containing 4,5-dichloro-2-methyl-4-isothiazolin-3-one in an amount of less than 100 ppm:

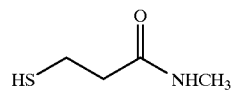
(A-1)

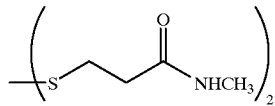
(A-2)

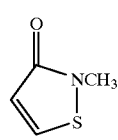
(I)

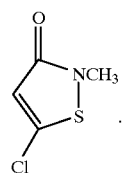
(II)

2. The process according to claim 1 wherein the mixture contains less than 20 ppm of 4,5-dichloro-2-methyl-4-isothiazolin-3-one.

3. The process according to claim 1 wherein the mixture contains the compound (I) and the compound (II) in a molar ratio of 1:3 to 1:10.

4. The process according to claim 1 further comprising centrifuging the mixture of the compounds (I) and (II) obtained after the reaction to control the content of nitrosamine or nitrosamine precursors in the mixture to be less than 5 ppm.

5. The process according to claim 1 wherein the first organic solvent is selected from the group consisting of $C_{4-12}$ alkylesters, $C_{7-14}$ hydrocarbons, $XCH=CHX$, $CH_2=CX_2$, $CX_2=CX_2$, $CHX=CX_2$, $C_{8-12}$ aromatic hydrocarbons and $C_6H_{(6-n)}X_n$ wherein n is an integer of 1 to 5 and X represents a halogen atom.

6. The process according to claim 1 wherein the compound of formula (A-1) or (A-2) is mixed with the first organic solvent in a weight ratio of 1:0.2 to 1:20.

7. The process according to claim 1 wherein the second organic solvent is selected from the group consisting of $C_{2-10}$ alkylethers, $C_{2-8}$ alkylesters, $C_{512}$ hydrocarbons, $CH_2X_2$, $CHCX_3$, $CX_4$, $CH_3CX_3$, $CH_2XCH_2X$ (wherein X represents a halogen atom) and $C_{6-10}$ aromatic hydrocarbons.

8. The process according to claim 1 wherein sulfuryl chloride is mixed with the second organic solvent in a weight ratio of 1:1 to 1:20.

9. The process according to claim 1, wherein the first and the second solvents are employed in a combination of $C_6H_{(6-n)}X_n$ and a $C_{4-6}$ alkylester, of $C_2H_nX_{4-n}$ and $CH_nX_{4-n}$, and of a $C_{4-6}$ alkylester and a $C_{6-10}$ aromatic hydrocarbon, respectively, wherein X is a halogen atom and n is an integer of 1 to 5.

10. The process according to claim 2 further comprising centrifuging the mixture of the compounds (I) and (II)

obtained after the reaction to control the content of nitrosamine or nitrosamine precursors in the mixture to be less than 5 ppm.

11. The process according to claim 3 further comprising centrifuging the mixture of the compounds (I) and (II) obtained after the reaction to control the content of nitrosamine or nitrosamine precursors in the mixture to be less than 5 ppm.

12. The process according to claim 5 wherein the compound of formula (A-1) or (A-2) is mixed with the first organic solvent in a weigh ratio 1:02.2 to 1:20.

13. The process according to claim 7 wherein sulfuryl chloride is mixed with the second organic solvent in a weight ratio of 1:1 to 1:20.

* * * * *